United States Patent [19]

Heim et al.

[11] 4,123,227
[45] Oct. 31, 1978

[54] METHOD AND APPARATUS FOR EVALUATING CHANGES IN INDICATOR TUBES

[75] Inventors: Ulrich Heim, Reinfeld; Kurt Leichnitz, Gross Grönau; Peter Wiesner, Ratekau, all of Germany

[73] Assignee: Drägerwerk Aktiengesellschaft, Lübeck, Germany

[21] Appl. No.: 809,674

[22] Filed: Jun. 24, 1977

[30] Foreign Application Priority Data

Jun. 26, 1976 [DE] Fed. Rep. of Germany ....... 2628790

[51] Int. Cl.² .................. G01N 21/26; G01N 21/28; G01N 31/06
[52] U.S. Cl. ........................... 23/232 R; 250/577; 422/86; 422/98
[58] Field of Search ............ 23/232 R, 254 R, 254 E, 23/253 TP; 73/23.1, 293; 116/114 AM; 250/565, 577

[56] References Cited

U.S. PATENT DOCUMENTS

| 2,594,514 | 4/1952 | Sweet | 23/232 R UX |
|---|---|---|---|
| 2,800,397 | 7/1957 | Offutt et al. | 23/232 R |
| 3,603,954 | 9/1971 | Takeuchi | 23/254 E X |
| 3,662,176 | 5/1972 | Kamentsky | 250/565 |
| 3,740,143 | 6/1973 | Groner et al. | 250/565 X |
| 3,932,132 | 1/1976 | Hijikata | 23/253 TP X |
| 3,990,849 | 11/1976 | Lee et al. | 23/253 TP UX |
| 4,003,707 | 1/1977 | Lubbers et al. | 23/232 R |
| 4,023,930 | 5/1977 | Blunck et al. | 23/232 R |

FOREIGN PATENT DOCUMENTS 2,113,711 3/1971 Fed. Rep. of Germany ............. 73/293

Primary Examiner—Morris O. Wolk
Assistant Examiner—Michael S. Marcus
Attorney, Agent, or Firm—McGlew & Tuttle

[57] ABSTRACT

Device for determining variations within an indicator tube having a material which varies in light intensity or color in the presence of particular gases, comprises a first set of light barrier devices as light sources and photoelectric cells on respective sides of the tube. A reference set of light barrier means is provided for sensing a reference value of light through the tube and is connected to a comparator for sensing the variations between it and the first set of light barrier tubes and for recording this information on a counter. The counters are connected to a time signal transmitter and time signal receiver and the predetermined variations which occur at various time intervals are picked up by an indicator or alarm circuit designed to show the variations and indications which are sensed in a particular time period. A method of gas measuring and warning using the light barriers disposed at spaced locations along the lengths of the indicator tube which has the substance therein which varies in light intensity or color, in accordance with the gas of a preselected type which is detected, when passed through the material therein, comprises converting the intensity of the light which is passed through the tube at the locations of the barriers into a logic signal, alternately storing the logic signals into two separate counters, periodically sensing the difference of the values in the counters, and using the sensed difference to start a time signal transmitter and time signal receiver. The time signal is monitored so that a new difference of the counters operates an alarm. The reciprocal of the value of the time signal sensed by the receiver may be used as an indication of the gas concentration.

10 Claims, 3 Drawing Figures

METHOD AND APPARATUS FOR EVALUATING CHANGES IN INDICATOR TUBES

FIELD AND BACKGROUND OF THE INVENTION

This invention relates in general to gas indicating devices and, in particular, to a new and useful device for, and method of gas measuring and warning, with the use of indicator tubes and by means of light.

DESCRIPTION OF THE PRIOR ART

The so-called indicator tubes filled with a pulverulent or granular chemical reagent in general serve the purpose of determining gaseous components in gas mixtures which are directed by suction or pressure through the tube. During this process, the content of the tube takes on color gradually in the direction of the gas flow. The length of the colored zone is proportional to the amount of the gas component to which the reagent is specifically responsive and which has flowed through the tube. In instances where the amount of the carrier gas directed by suction or pressure through the tube is known, the percentage of contamination of the carrier gas with the specific gas component can be inferred from the length of the colored zone.

Such tubes are used for both single tests and, in connection with a gas feed pump, for long-term monitoring. In any case, information is obtained on the amount of the gas to be measured which has passed into the tube. Particularly in long-term monitoring, the length of the colored zone read at the end of the monitoring period is a measure for the gas concentration of the gas to be measured, averaged over this entire period. In many instances, however, it is important to know whether at some point of time during the monitoring period, peak values of concentration occur, in order to be able to instantly start an alarm in cases where critical concentration values are exceeded.

A known device for determining and registering the content of certain components in air or other gases makes it possible to determine the instantaneous concentration for shorter monitoring periods. In this device, indicator tubes which are already opened and which are accommodated in a magazine are placed successively into the air current to be tested. The magazine is automatically shifted or indexed by means of a switching mechanism, such as a switch clock, in definite periods of time and so that a single new indicator tube is always placed in the path of the air current. The tube remains in this position until the air feeding device has accomplished the provided operation of directing the air current through the indicator tube under predetermined conditions.

Mechanically, this device is very complicated. The measured values are determined by observation by the operator and thus, the results depend on the skill of the respective person. A further disadvantage is that an alarm cannot be automatically started. (see German Pat. No. 1,093,113).

In another known device for detecting gas concentrations, particularly CO concentrations in air, an optical and/or acoustic signal is delivered after a certain period of time upon a predetermined gas concentration indicated by a color change of the reactive layer. The device comprises a motordriven pump, a mount for an indicator tube at the suction or pressure side of the pump, and a photoelectric sensing unit. This unit is disposed so as to scan a definite area of an indicator tube placed in the mount. The current delivered by the photosensitive element upon a variation of the intensity of the light beam directed on and reflected from the scanned area starts an optical and/or acoustic alarm. With this device, the total amount of the foreign gas directed through the indicator tube and corresponding to the length of the color change is measured, and a warning system may be based thereon. The instantaneous concentration of this gas in the air to be measured is not determined. Just this concentration, however, is decisive. The physiological effectiveness of toxic matters does not depend only on the absorbed quantity, but depends very strongly on the concentration also. This is why a measuring of the amount alone may become futile. (German Offenlegungsschrift No. 1,598,021).

Another known method of measuring the CO concentration by means of indicator tubes utilizes the coloring of a reaction gel in the presence of CO in the air directed through the indicator tube. In this design, the indicator tube is placed in the path of rays of a spectrophotometer. This measures the time necessary for obtaining a definite attenuation of the radiation as the rays penetrate the coloring layer of the reaction gel. This time is a function of the CO concentration in the air directed through the indicator tube.

This method is disadvantageous since quality reaction gels are needed ensuring constantly identical and uniform coloring of the entire layer. The hue to be measured, which is a criterion for the CO concentration, may easily be influenced by foreign light. In long-term monitoring, only an integral measurement, thus, the determination of a mean value, is possible. Concentration peaks or depths cannot be detected, (see "A clinical Method for the Determination of Carbon Monoxide in Air," Tore Andersson and Hans Dahlstrom, "Science Tools," April 1958).

SUMMARY OF THE INVENTION

The present invention is directed to a method and device which makes it possible to determine the concentration of gases to be measured even at a point in the course of long-term monitoring operations by means of indicator tubes, and to indicate the mesured values and-/or give an alarm as soon as limit values are exceeded or have not been attained.

In accordance with the invention, the intensity of the light is determined periodically, in interrogation cycles, from light barriers which are disposed perpendicularly to the indicator tube axis and spaced from each other, converted into logic signals and alternately stored in two counters. When there is any difference between the contents of the two counters, a time-signal transmitter and a time-signal receiver are started. If there is any new difference between the counter contents resulting from the subsequent interrogations and occurring during the running period of the time-signal transmitter, an alarm is started. The gas concentration is determined by the reciprocal value of the elapsed period of time recorded by the time-signal receiver.

The advantages obtained with this method and apparatus are primarily that even in long-term monitoring processes, the concentration can be read at any time and, further, there is the possibility of starting an alarm even in response to rapidly varying concentrations, the peaks of which can be predetermined.

The device for gas measuring and warning comprises a clamping mechanism for the indicator tubes, light barriers at locations which are spaced from each other, a reference light barrier, an intrrogation circuit, an evaluating unit, and an indicating unit. The device is capable of detecting even peak values securely and rapidly due to the possible fine subdivision of the range of measurement. After a warning, the indicator tube can still be employed for measuring, until it is completely used. This is an advantage of great economic value for long-term monitoring. The alarm threshold can be changed without any mechanical means simply by adjusting the time-signal transmitter.

In a variation of the inventive construction, instead of the transmitted light of the light barriers, the intensity of a reflected light from transmitter and detector units provided at locations spaced from each other may be utilized for determining the coloration. Such a design may be advantageous in cases where the light transmittance of the material in the indicator tube is not satisfactory. A material of this nature may be needed for certain gases to be measured with the aid of indicator tubes.

Accordingly, an object of the invention is to provide an improved method of gas measuring and warning using light barriers disposed at spaced locations along the length of an indicator tube which has a substance therein which varies in light intensity and/or color in accordance with the gas of a preselected type which is passed through the material therein, which comprises converting the intensity of light which is passed through the tube at the locations of the barriers into a logic signal, alternately storing the logic signals into two separate counters, periodically sensing the difference in values of the two counters and using the sensed difference to start a time-signal transmitter and a time-signal receiver and, whenever a new difference of the counters results therefrom, for effecting the starting of an alarm and also using the reciprocal of value of the time-signal receiver to indicate gas concentration.

Another object of the invention is to provide a device for determining values of a gas passed through an air indicating tube which has an indicating material therein which changes in intensity and/or color in response to the various gases which are to be sensed and which comprises at least one first light barrier adjacent the indicator tube providing means for sensing variations in light intensity through the tube and the material therein, and including at least one reference light barrier for sensing a reference light condition through the tube which are connected to comparator means for sensing variations between successive readings and, wherein, the comparator is connected to an evaluating means for indicating selected variations between the two counters.

A further object of the invention is to provide a device for determining values of a gas passed through air indicating tubes and similar device, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

DESCRIPTION OF THE PREFERRED EMBODIMENT

Figure 1:
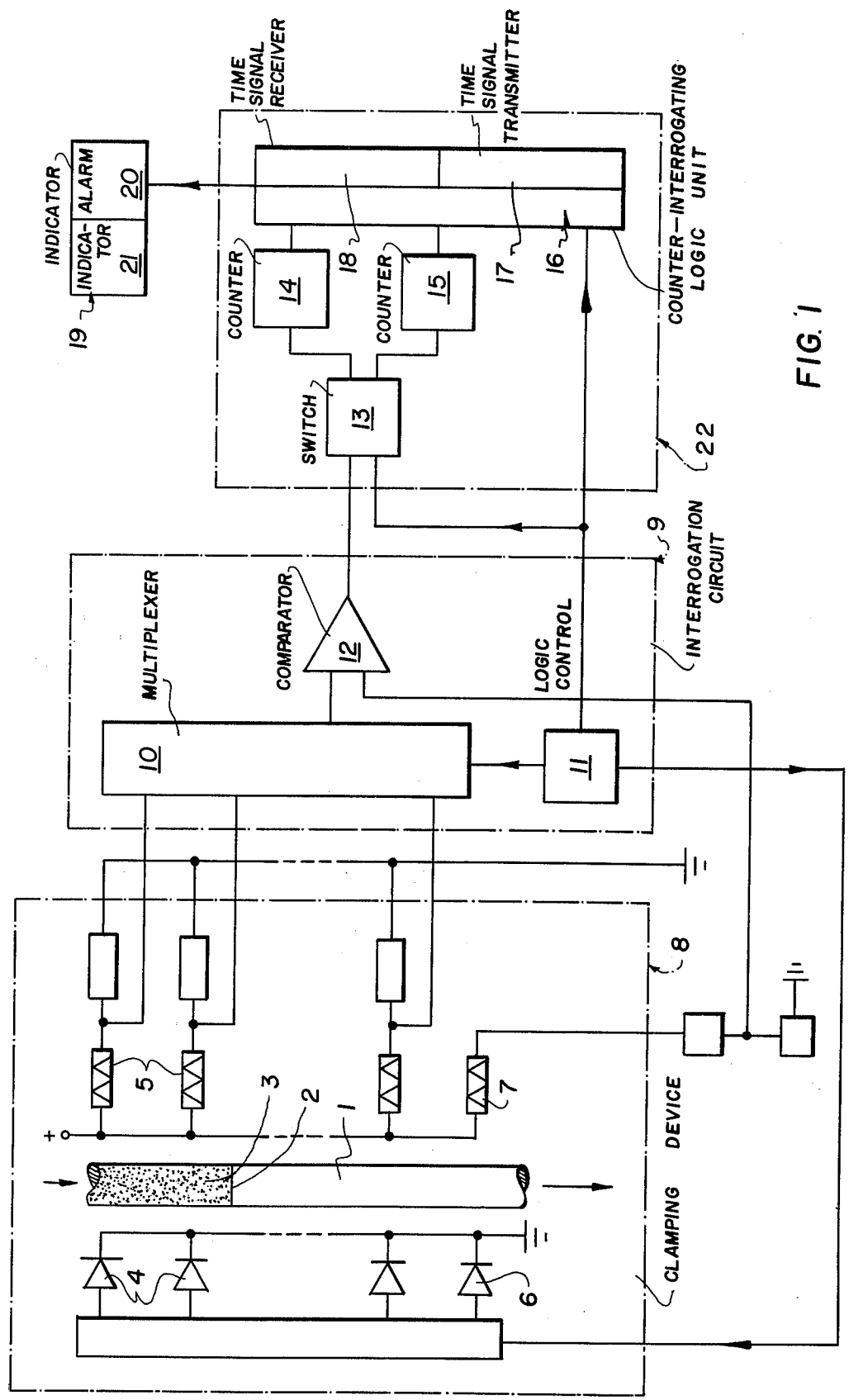
FIG. 1 is a schematic diagram of a system for gas measuring and warning, constructed in accordance with the invention.

Referring to the drawings in particular, the invention embodied therein, comprises a method and a device for evaluating colorations or light intensity variations in indicator tubes of a type which has a material 3 which is disposed in the indicator tube 1 and through which gas is passed in order to act upon the material and cause color and/or light intensity variations thereof.

Figure 2:
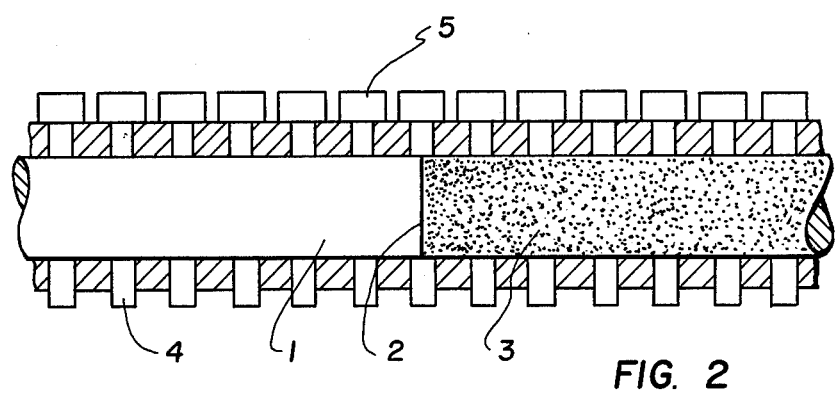
FIG. 2 is partial enlarged sectional view of an indicator tube having a sensing material therein which varies in accordance with a gas which is passed therethrough.
Figure 3:
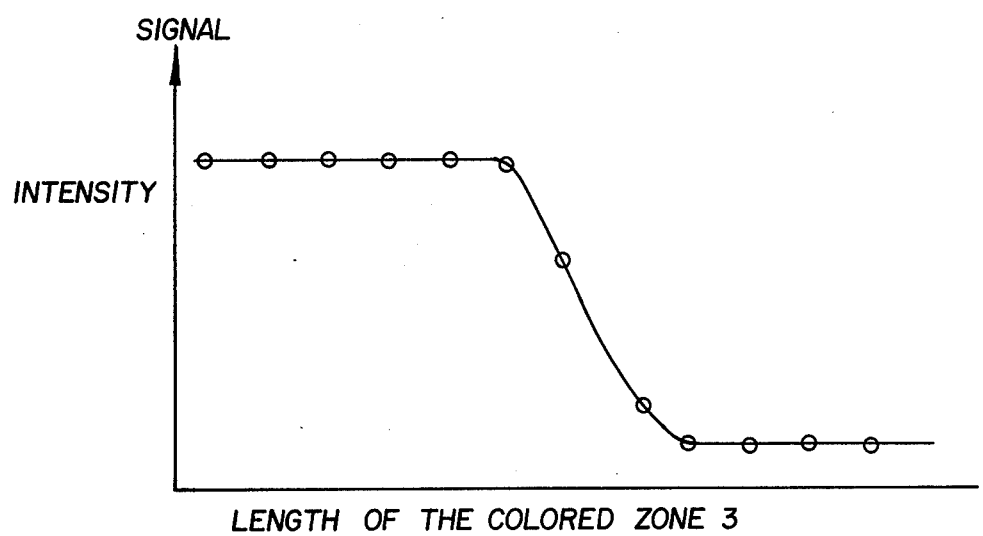
FIG. 3 is a curve indicating variation and signal intensity over the length of the colored zone of the material within the indicating tube.

By means of the device for gas measuring and warning, the arrangement of which is shown in FIG. 1, the specific gas to be detected in an indicator tube and contained in the air to be monitored, is directed by pressure or suction through the tube. The gas concentration is determined by the reaction of material 3 in the tube, and as soon as certain limit values are exceeded, an alarm is started. To this end, as may be seen from FIGS. 2 and 3, which are oriented in interrelated views, the travel velocity v beginning at an end or front 2 of the colored zone 3 of indicating material in the tube 1 is picked up during the entire monitoring or measuring operation. There is a predetermined threshold value for the travel velocity $v$ and, if this threshold is exceeded, the alarm is started. In addition, or even alone, the respective, instantaneous, travel velocity $v$, reflecting the concentration, may be indicated.

The travel velocity $v$ of colored zone 3 is picked up by means of light barriers means formed across tube 1 by elements 4 and 5, each comprising an optical transmitter, such as a light-emitting diode 4, and a detector 5, which are arranged at spaced locations along the axis of the indicator tube. A single light source may also be substituted for diodes 4. The intensity of the light from diodes 4 is converted, by comparison with the threshold value from a reference light barrier means formed by 6 and 7 located at a control location along the tube 1, into a yes-or-no signal. This signal is based on the information on the coloration of the reaction material which took place in the indicator tube.

Light barriers 4 and 5 which are spaced from each other, and reference light barrier 6 and 7 are accommodated in a mechanical clamping device 8, and they are arranged alongside and connected to an interrogation circuit 9 which, in turn, is alongside and connected to an evaluating unit 22. Interrogation circuit 9 comprises a multiplexer 10, a logic control element 11 and a comparator 12. Evaluating unit 22 comprises, after a switch 13, parallel connected counters 14 and 15 which are both connected to a counter-interrogating logic unit 16. A time-signal transmitter 17 and a time-signal receiver 18 are the elements of counter-interrogating unit 16.

An indicating unit 19 comprising an alarm signal transmitter 20 and an indicator 21 receives its values from counter-interrogating logic unit 16.

The monitoring operation takes place in interrogation cycles which are controlled from interrogation circuit 9 and in the course of which light-emitting diodes 4 are successively triggered and detectors 5 associated therewith are sequentially interrogated. The detected 37 yes" signals are stored in one of the counters, for example, in counter 14, depending on the position of switch 13. The number of "yes" signals detected in the immediately following interrogation cycle is then stored in counter 15, upon switching of switch 13. In the next following cycle, the number of "yes" signals is again supplied to counter 14, whereby, the previous content thereof is erased. In this way, the number of "yes" signals detected by interrogation in the individual cycles is alternately entered into the two counters 14 and 15.

On completion of each cycle, the two counter contents are compared with each other through counter-interrogating logic unit 16. Every time the number of yes signals stored in one of the counters is greater than in the other counter, time-signal transmitter 17 and time-signal receiver 18 are started. Time-signal transmitter 17 runs during a fixedly adjustable period of time, and upon expiration thereof, is reset to zero and brought into a stand-by position. Should the counter-interrogating logic unit 16, within the period of run of time-signal transmitter 17, again determine that the contents stored in the two counters 14 and 15 differ from each other, an alarm is started through alarm signal transmitter 20 or another corresponding action is set off. By adjusting the running time of time-signal transmitter 17, a minimum period of time can be set. The travel time of the color front 2 in tube 1 from one detector to the next one must not fall short of this set minimum or the alarm will sound.

Time-signal receiver 18 continues running until counter-interrogating logic unit 16 again determines an inequality in the counter contents, irrespective of whether this occurs within or outside the running time of time-signal transmitter 17. With an inequality in the number of yes signals, the two time-signal elements are reset to zero again (time-signal transmitter 17 is reset only if it is not yet run down) and immediately restarted. Prior to zeroing time-signal receiver 18, however, the period of time which elapsed since its last zeroing is interrogated and the reciprocal value thereof is formed. This reciprocal value of the elapsed time, which corresponds to the travel time of the color front between two detectors 5, is directly proportional to the mean gas concentration present during the running time of time-signal receiver 18. This concentration is indicated by indicator 21.

In operation, light coming from light sources 4 is directed through the tube 1 and sensed by light detectors 5. Signals from light detectors 5 are then fed through multiplexer 10 and the signals from multiplexer 10 are then fed to the comparator 12. Simultaneously with this, light is directed across tube 1 from reference light source 6 to reference barrier 7. Reference barrier 7 produces a signal through circuitry shown only as a block to the comparator 12. The circuitry connected to reference barrier 7 is of a type to form a signal which is compatible with the signal formed by multiplexer 10. Comparator 12 then compares the light intensity signal from the detectors 5 with the light intensity signal from the reference 7 to produce yes or no signals that are fed to the switch 13. A yes signal, for example, is produced when a barrier formed by a light source 4 and detector 5 combination directs light across a section of tube 1 through which the edge 2 has not yet passed. The logic control 11 is utilized to standardize the operation of the various elements in the inventive structure and is connected to the light sources 4 and 6, the multiplexer 10 and the counter interrogating logic unit 16.

This makes it possible to determine the present concentration of the gas to be monitored any time during the monitoring operation. Upon a too rapid increase of this concentration, an alarm is started to warn the crew or plant.

While a specific embodiment of the invention has been shown and described in detail to illustrate the application of the principles of the invention, it will be understood that the invention may be embodiment otherwise without departing from such principles.

What is claimed is:

1. A method of gas measuring and warning using light barriers one of which is a reference light barrier located at spaced locations along the length of an indicator tube which has a substance therein which varies in light intensity and/or color to provide a gas value in accordance with a gas of a preselected type which is passed therethrough and wherein the light barriers are formed by a light source for directing light across the indicator tube and a light detector for sensing the light, comprising directing a gas to be measured through the indicator tube, directing light from the light source of the barriers through the indicator tube and sensing the intensity of the light which is passed through the indicator tube with the light detectors at the locations of the barriers, converting the light intensity sensed at the barriers into a logic signal by continuously comparing the light intensity sensed at the reference light barrier with that sensed at the remaining light barriers, alternately storing the sensed logic signals into two separate counters, periodically determining the difference of the values in said two counters and using the determined difference to start a time signal transmitter and a time signal receiver, and whenever a new difference of the counters results from subsequent determinations of the difference in the counters which new difference produces a new signal, using the new signal to start an alarm.

2. A method of gas measuring and warning, according to claim 1, including determining the reciprocal of the indication received at the time signal receiver to indicate gas concentration.

3. A method of gas measuring and warning, according to claim 1, wherein two counters are employed, and including alternately feeding the logic signal to one and then to the other of said counters.

4. A method of gas measuring and warning, according to claim 3, wherein variations of successive readings are noted for each of said counters to generate a signal which is effective to operate said time signal transmitter and said time signal receiver and using the time signal receiver signal to actuate an alarm.

5. A device for determining the type of a gas passed through an indicating tube having a gas indicating material therein which changes in respect to light evaluations in response to various types of gases, comprising an indicator tube having a passage therethrough for the gas to be typed, a gas indicator material in said tubes, at least one first light barrier means adjacent said indicator tube including a light source and means for sensing variations in light intensity from said light source through said tube and said gas indicator material therein, at least one reference light barrier means adjacent the indicator tube and spaced away from said first light barrier means including a reference light source, and reference means for sensing a reference light condition through said indicator tube, a multiplexer connected to said first light barrier means, comparator means connected to said reference light barrier means and said multiplexer for sensing variations between said first and second light barrier means, and evaluating means connected to said comparator means for indicating selected variations, said evaluating means comprising a switch, first and second counters connected to said switch, and a counter-interrogating logic unit connected to said first and second counters and having a time signal transmitter and a time signal receiver, said indicator unit comprising an alarm signal transmitter and an indicator.

6. A device for determining the type of a gas passed through an indicating tube having a gas indicating material therein which changes in respect to light evaluations in response to various types of gases, comprising an indicator tube having a passage therethrough for the gas to be typed, a gas indicator material in said tube, at least one first light barrier means adjacent said indicator tube including a light source for directing light through said indicator tube and said gas indicator material therein and means for sensing variations in the intensity of the light from said light source, at least one second reference light barrier means adjacent the indicator tube and spaced away from said first light barrier means including a reference light source and reference means for sensing a reference light condition through said indicator tube, a multiplexer connected to said first light barrier means, comparator means connected to said second reference light barrier means and said multiplexer for sensing variations between said first and said second light barrier means, and evaluating means connected to said comparator means for indicating selected variations.

7. A device according to claim 6, wherein said evaluating means comprises a switch, first and second counters connected to said switch, and a counter-interrogating logic unit connected to said first and second counters and having a time signal transmitter and a time signal receiver.

8. A device according to claim 6 wherein said at least one first light barrier means comprises a light transmitter arranged on one side of said indicator tube for directing light across said indicator tube and a light detector arranged on an opposite side thereof for receiving and sensing the light from said light transmitter.

9. A device according to claim 8, including a plurality of light transmitters and light detectors arranged along the length of said indicating tube on respective opposite sides thereof.

10. A device according to claim 8, wherein said reference light barrier means includes a plurality of light transmitter and detector units arranged in parallel relation to each other and at spaced locations along the length of said indicating tube.

* * * * *